(12) United States Patent
Finch et al.

(10) Patent No.: US 6,685,694 B2
(45) Date of Patent: *Feb. 3, 2004

(54) METHODS AND KITS FOR LOCKING AND DISINFECTING IMPLANTED CATHETERS

(75) Inventors: Charles D. Finch, Clinton, MS (US); Paul F. Marad, Andover, MA (US); John Wang, Sammamish, WA (US); James M. Brugger, Newburyport, MA (US)

(73) Assignee: Vasca, Inc., Tewksbury, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/859,886

(22) Filed: May 16, 2001

(65) Prior Publication Data

US 2002/0010438 A1 Jan. 24, 2002

Related U.S. Application Data

(63) Continuation-in-part of application No. 09/611,421, filed on Jul. 7, 2000, which is a continuation-in-part of application No. 09/359,842, filed on Jul. 23, 1999, now Pat. No. 6,592,564.

(51) Int. Cl.[7] .............................................. A61M 31/00
(52) U.S. Cl. ...................... 604/508; 604/523; 604/500; 604/256; 604/93.01; 604/537
(58) Field of Search ........................... 604/500, 19, 27, 604/28, 48, 508, 513, 502, 522, 93.01, 256, 523, 288.01, 264–266, 269, 36, 181, 183; 514/222.5, 720, 721; 206/363–365, 438

(56) References Cited

U.S. PATENT DOCUMENTS

| | | | |
|---|---|---|---|
| 4,069,185 A | * | 1/1978 | Sullivan ..................... 523/112 |
| 4,107,305 A | | 8/1978 | Pfirrmann |
| 4,445,889 A | | 5/1984 | Wong et al. |
| 4,587,268 A | | 5/1986 | Pfirrmann |
| 4,626,536 A | | 12/1986 | Pfirrmann |
| 4,797,282 A | | 1/1989 | Wahlig et al. |
| 4,853,225 A | | 8/1989 | Wahlig et al. |
| 4,929,242 A | | 5/1990 | Desecki et al. ............. 604/266 |

(List continued on next page.)

FOREIGN PATENT DOCUMENTS

| WO | WO 00/01391 | 1/2000 | .......... A61K/31/54 |
|---|---|---|---|

OTHER PUBLICATIONS

Darouiche, R.O. and Raad, I.I. (1997). "Prevention of catheter–related infections: the skin," Nutrition 13(4)(suppl):26S–29S.

(List continued on next page.)

Primary Examiner—Brian L. Casler
Assistant Examiner—Cris L. Rodriguez
(74) Attorney, Agent, or Firm—Townsend and Townsend and Crew LLP

(57) ABSTRACT

Implanted catheters are locked with a solution comprising a lower alcohol, typically ethanol, propanol, or butanol, in a range from 1% to 99% by volume, and an additive in a range from 1% to 99% by volume, the additive comprising an anti-microbial, typically taurolidine or triclosan, or an anti-coagulant, typically riboflavin, sodium citrate, ethylene diamine tetraacetic acid, or citric acid. The use of an alcohol and additive solution can effectively reduce fouling of the catheter, particularly clotting and thrombus in intravascular catheters, as well as eradicate existing infections and/or reduce the risk of potential infections. Existing infections and/or potential infections can be further reduced by employing a catheter body which permits an anti-microbial solution to penetrate into the catheter body and preferably through the catheter into tissue surrounding the implanted catheter.

34 Claims, 10 Drawing Sheets

U.S. PATENT DOCUMENTS

| | | | |
|---|---|---|---|
| 4,954,239 A | * 9/1990 | Mueller | 206/210 |
| 4,960,415 A | 10/1990 | Rüinmuller | |
| 5,053,021 A | 10/1991 | Feibus | 604/264 |
| 5,077,281 A | 12/1991 | Reinmuller | 514/56 |
| 5,093,117 A | 3/1992 | Lawrence et al. | |
| 5,142,010 A | * 8/1992 | Olstein | 424/407 |
| 5,174,990 A | * 12/1992 | Douglas | 424/53 |
| 5,210,083 A | 5/1993 | Pfirrmann | |
| 5,263,930 A | 11/1993 | Ensminger | |
| 5,281,205 A | 1/1994 | McPherson | |
| 5,358,492 A | * 10/1994 | Feibus | 604/264 |
| 5,362,754 A | 11/1994 | Raad et al. | |
| 5,458,583 A | * 10/1995 | McNeely et al. | 604/103.13 |
| 5,545,213 A | 8/1996 | Keogh et al. | |
| 5,593,665 A | 1/1997 | Pfirrmann et al. | |
| 5,688,516 A | * 11/1997 | Raad et al. | 424/405 |
| 5,704,915 A | 1/1998 | Melsky et al. | |
| 5,718,899 A | 2/1998 | Gristina et al. | |
| 5,752,941 A | 5/1998 | Romano' et al. | |
| 5,772,640 A | 6/1998 | Modak et al. | 604/265 |
| 5,783,570 A | 7/1998 | Yokota et al. | |
| 5,788,979 A | 8/1998 | Alt et al. | |
| 5,807,356 A | 9/1998 | Finch, Jr. et al. | 604/284 |
| 5,931,829 A | 8/1999 | Burbank et al. | 604/502 |
| 5,954,239 A | 9/1999 | Evans et al. | |
| 5,954,691 A | 9/1999 | Prosl | |
| 5,989,239 A | 11/1999 | Finch et al. | 604/502 |
| 5,997,524 A | 12/1999 | Burbank et al. | 604/506 |
| 6,007,516 A | 12/1999 | Burbank et al. | 604/93 |
| 6,042,569 A | 3/2000 | Finch, Jr. et al. | 604/175 |
| 6,056,717 A | 5/2000 | Finch et al. | 604/93 |
| 6,059,766 A | 5/2000 | Greff | 604/515 |
| 6,063,061 A | * 5/2000 | Wallace et al. | 424/423 |
| 6,120,492 A | 9/2000 | Finch et al. | 605/502 |
| 6,132,415 A | 10/2000 | Finch et al. | 605/502 |
| 6,146,373 A | * 11/2000 | Cragg et al. | 604/19 |
| 6,159,232 A | * 12/2000 | Nowakowski | 606/213 |
| 6,166,007 A | 12/2000 | Sodenann | |
| 6,193,684 B1 | 2/2001 | Burbank et al. | 604/29 |
| 6,206,851 B1 | 3/2001 | Prosl | |
| 6,248,343 B1 | * 6/2001 | Jampani et al. | 424/405 |
| 6,299,609 B1 | 10/2001 | Finch et al. | |
| 6,299,610 B1 | * 10/2001 | Finch et al. | 604/500 |
| 6,350,251 B1 | * 2/2002 | Prosl et al. | 514/222.5 |
| 6,361,524 B1 | * 3/2002 | Odell et al. | 604/181 |

OTHER PUBLICATIONS

Gorman, S.P. et al. (1987). "A comparative study of the microbial antiadherence capacities of three antimicrobial agents," *J. Clin. Pharm. Ther.* 12:393–399.

Jones, D.L. et al. (1991). "The effects of three non–antibiotic, antimicrobial agents on the surface hydrophobicity of certain micro–organisms evaluated by different methods," *J. Appl. Bacteriol.* 71:218–227.

Root, J.L. et al. (1988), "Inhibitory effect of disodium EDTA upon the growth of Staphylococcus epidermidis in vitro: relation to infection prophylaxis of Hickman catheters," *Antimicrob. Agents Chemother.* 32(11):1627–1631.

Sodemann, K. et al. (1997). "Gentamicin/sodium–citrate mixture as antibiotic–lock technique for salvage and prevention of catheter–related infections– A four year trail," *Journal of the American Society of Nephrology*, Vol 8, Sep. 1997, p. 173A.

Traub, W.H. et al. (1993). "Taurolidine: in vitro activity against multiple–antibiotic–resistant, nosocomially significant clinical isolates of *Staphylococcus aureus, Enterococcus faecium*, and diverse Enterobacteriaceae," *Chemotherapy* 39:322–330.

Willatts, S.M. et al. (1995). "Effect of the antiendotoxic agent, taurolidine, in the treatment of sepsis syndrome: a placebo–controlled, double–blind trial," *Crit. Care Med.* 23(6):1033–1039.

* cited by examiner

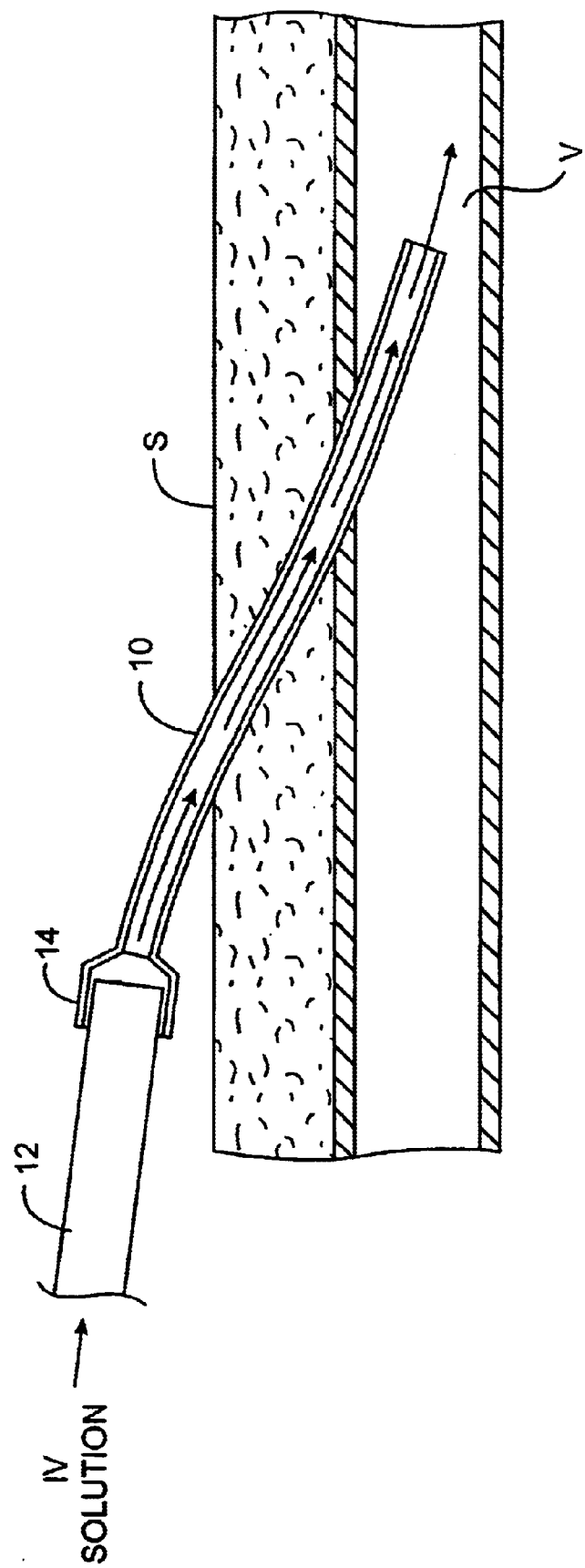

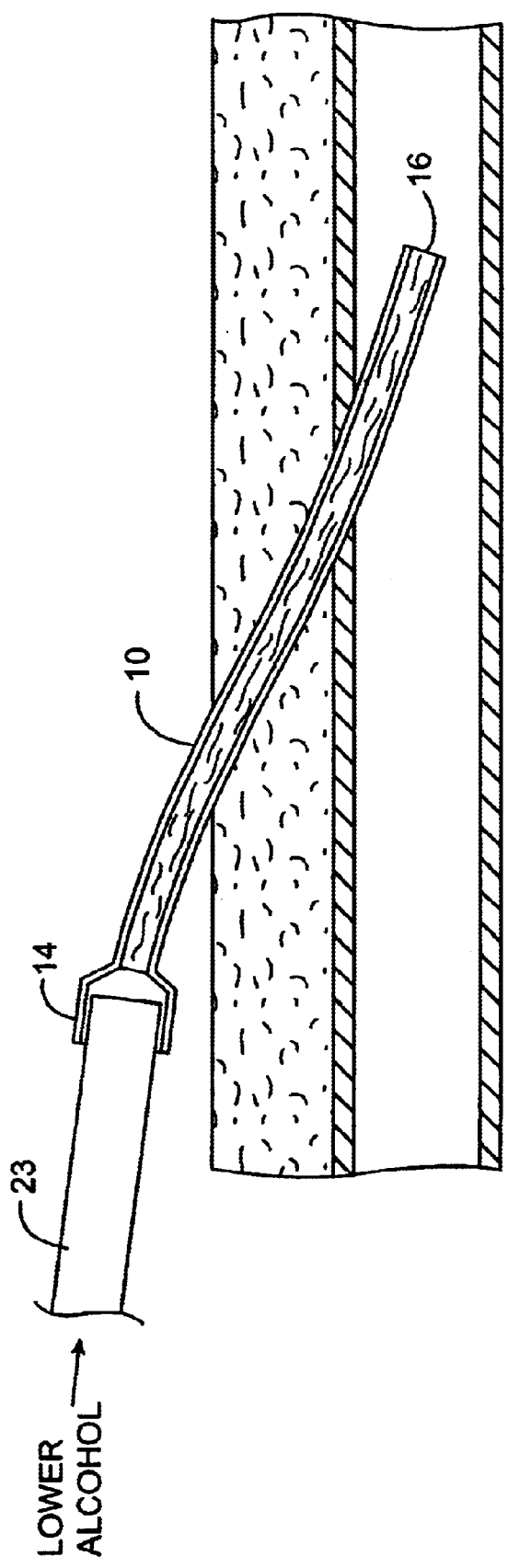

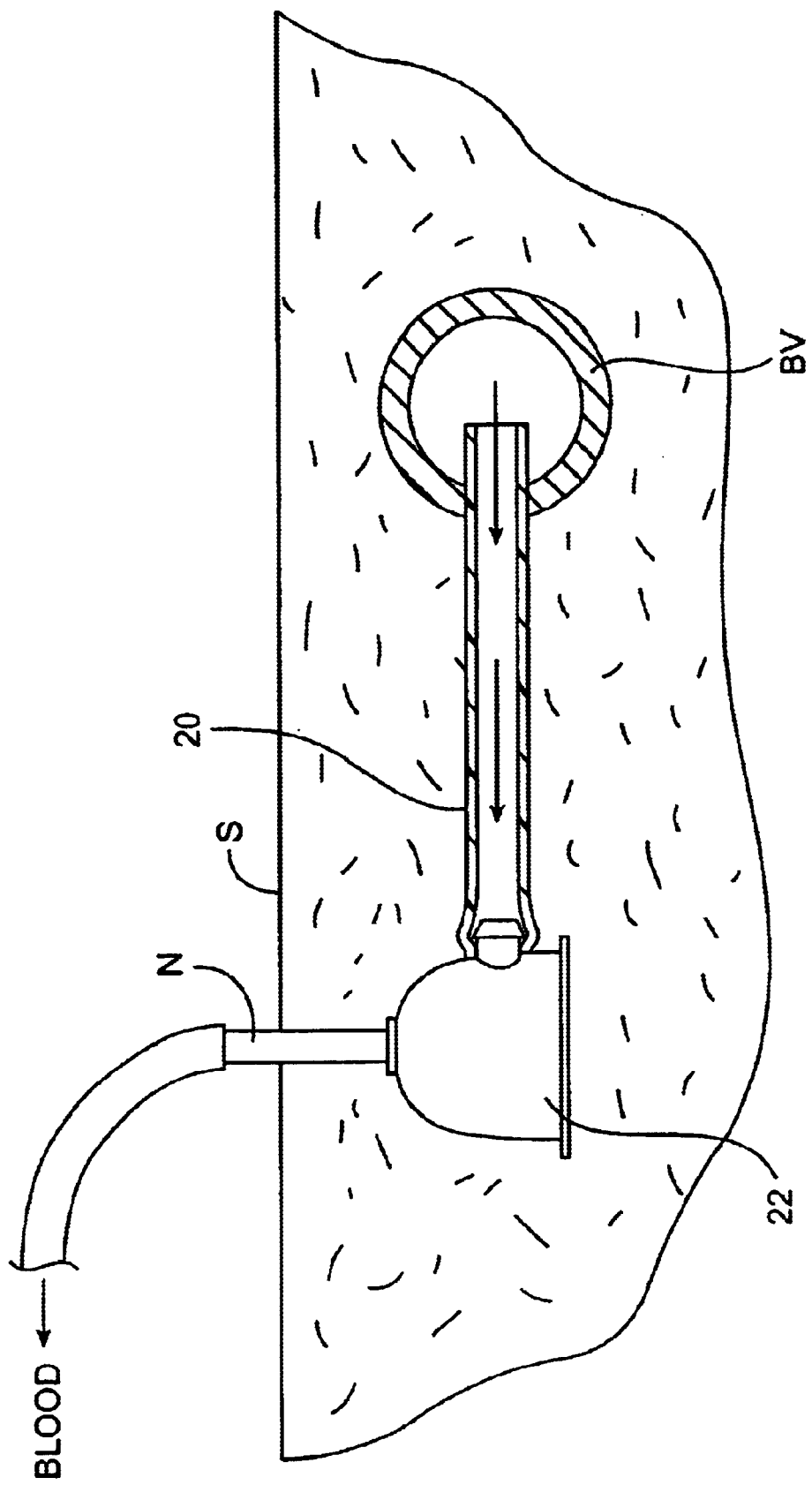

METHODS AND KITS FOR LOCKING AND DISINFECTING IMPLANTED CATHETERS

CROSS-REFERENCES TO RELATED APPLICATIONS

This application is a continuation-in-part of, and claims the benefit of priority from, U.S. patent application Ser. No. 09/611,421, filed Jul. 7, 2000, which was a continuation-in-part of U.S. patent application Ser. No. 09/359,842, filed Jul. 23, 1999, now U.S. Pat. No. 6,592,564 the full disclosures of which are incorporated herein by reference.

BACKGROUND OF THE INVENTION

1. Field of the Invention

The present invention relates generally to medical methods and kits. More particularly, the present invention relates to methods and kits for flushing an interior lumen of an implanted catheter prior to closing the catheter between successive uses.

Implanted catheters enjoy widespread use in a number of medical procedures. For example, intravenous (IV) therapy relies on long-term implantation of a venous catheter to deliver fluids, medications, and other substances to a patient. Hemodialysis and hemofiltration both rely on separate draw and return catheters implanted in a vein to allow extra corporeal treatment of the blood. Peritoneal dialysis, in contrast, relies on a single catheter implanted in the peritoneum to permit introduction and withdrawal of dialysate to permit in situ dialysis.

The need to leave catheters implanted over long periods of time raises a number of concerns. For example, the catheters can become infected requiring treatment of the patient and often times removal of the catheter. This is a particular problem with transcutaneous catheters where the skin penetration is a common route of infection. Secondly, implanted catheters can often become plugged or fouled over time. This is a particular problem with intravascular catheters where clotting and thrombus formation within the catheter lumen can be problematic.

To reduce problems associated with thrombus formation, it is now common to "lock" intravascular access catheters between successive uses. Locking typically involves first flushing the catheter with saline to remove blood and other substances from the catheter lumen. After the catheter has been flushed, an anti-coagulant solution, typically heparin, is then injected to displace the saline and fill the lumen. The heparin-locking solution both excludes blood from the lumen and actively inhibits clotting and thrombus formation within the lumen. While some thrombus may still form at the distal tip of the catheter, the formation is usually minimal and presents few problems. It has further been proposed to combine various anti-microbial substances with the locking solution in order to inhibit infection at the same time that thrombus is being inhibited.

While generally effective, the use of heparin locks suffers from a number of disadvantages. The need to prepare a heparin solution at the end of every catheter treatment session is time-consuming and presents an opportunity for error by a caregiver. Hemodialysis and hemofiltration patients will have to undergo such heparin locks at least several times a week, while patients on IV may have to undergo such heparin locks several times a day. Over time, the inconvenience and expense of performing heparin locks can build up. Moreover, the need to combine a separate anti-microbial agent in the heparin lock solution further complicates the procedure and adds expense, and the addition of an anti-microbial agent to the heparin lock will generally be effective only within the lumen and at the openings from the lumen. There will be little reduction in the risk of infection in the regions surrounding the implanted catheter, including at the point of penetration through the skin where the risk of infection is the greatest.

For all these reasons, it would be desirable to provide improved methods, compositions, and kits for locking implanted catheters between successive uses. Such locking methods should inhibit fouling of the catheter lumens and eradicate existing infections and/or reduce the chance of potential infections. In particular, such methods, compositions, and kits should be easy to implement, require minimum or no preparation, be of low cost, and be useful with most or all types of implanted catheters, including hemodialysis and hemofiltration catheters, IV catheters, peritoneal dialysis catheters, and the like. At least some of these objectives will met by the inventions described hereinafter.

2. Description of the Background Art

U.S. Pat. No. 4,929,242 describes a solution containing glycerol and having a density similar to that of blood for providing a heparin lock on an intravenous catheter. U.S. Pat. No. 5,077,281 describes an anti-microbial solution containing a taurolin compound for inhibiting coagulation in dialysis catheters and other vascular prostheses. PCT WO 00/01391 describes an anti-microbial lock comprising a taurinamide derivative. Commonly assigned U.S. Pat. Nos. 5,807,356; 5,931,829; 5,989,239; 5,997,524; 6,007,5165; 6,120,492; 6,132,415; and 6,193,684; and co-pending patent application Ser. Nos. 09/003,772; and 09/161,044, are relevant to the present application. All of the above patents and pending applications are incorporated herein by reference.

SUMMARY OF THE INVENTION

The present invention provides methods and kits for the improved locking and/or disinfection of subcutaneously and transcutaneously implanted catheters. The catheters typically will have a distal end which is open to a body lumen. Most commonly, the catheters will be intravascular catheters where the distal end is implanted in or attached to a blood vessel, usually a vein, but in some cases an artery. Exemplary intravascular catheters include hemodialysis and hemofiltration catheters, intravenous catheters, and the like. Intravenous catheters can be used for a wide variety of purposes, including fluid infusion, drug delivery, and the like. Catheters attached other than to the vasculature include peritoneal dialysis catheters which are open to the peritoneal cavity, and the like.

The catheters which are treated by the methods of the present invention may be transcutaneously implanted or subcutaneously implanted. By "transcutaneously implanted," it is meant that the distal end of the catheter is attached to or implanted within a target body lumen and a proximal end of the catheter is located externally to the patient. An intermediate portion of the catheter will thus pass through or penetrate the patient's skin, and the proximal end of the catheter will usually have a hub to permit selective attachment of infusion tubes, syringes, solution bags, and the like. Most commonly, the proximal attachment hub will have a luer fitting. By "subcutaneously implanted," it is meant that the entire catheter is implanted beneath the skin and no portion of the catheter extends through the skin. Such subcutaneously implanted catheters are typically attached to a fully implanted hub at their proximal ends. The hub permits percutaneous access via a needle or other penetrating element. After a treatment session is finished, the needle or other penetrating element is removed and all portions of the catheter and proximal hub are then located beneath the skin. Examples of such subcutaneously implanted catheters and proximal access hubs are described in the commonly assigned, copending applications described above, as well as U.S. Pat. No. 5,807,356, the full disclosures of which have previously been incorporated herein by reference.

As described in the Background section above, both transcutaneously and subcutaneously implanted catheters are subject to fouling and plugging, particularly in and about their distal ends which are implanted in or attached to a blood vessel or other body lumen. To reduce the risk of such fouling, the present invention provides methods, compostions, and kits for filling a lumen of the implanted catheter with a solution of a lower alcohol and an additive. The lower alcohol is typically ethanol, propanol, or butanol, with isopropanol being the preferred alcohol. Surprisingly, it has been found that these lower alcohols are effective in inhibiting fouling and plugging of the lumen, particularly in inhibiting clot formation within the lumens of intravascular catheters. The ability to inhibit clot formation without the need to prepare and use heparin solutions is a significant advantage. Moreover, the lower alcohols have the additional ability to eradicate existing infections and/or inhibit potential infections. The additive may comprise either an anti-microbial substance, typically taurolidine or triclosan, or an anti-coagulant substance, typically riboflavin, sodium citrate, ethylene diamine tetraacetic acid, or citric acid. This solution combination of a lower alcohol and an additive is particularly effective since alcohol increases the effectiveness of the anti-microbial or anti-coagulant additives, while the additives in return reduce the possible toxic effects of the alcohol. Thus, both the reduction of catheter fouling and the eradication and/or inhibition of infection can be achieved with the use of commonly available, widely accepted materials which are introduced to the catheter lumen in a convenient fashion, as described in more detail below.

The ability to eradicate existing infections and/or inhibit potential infections of the implanted catheter can be improved by utilizing catheters where at least a portion of the catheter body permits the lower alcohol to permeate the catheter body and, preferably, pass outwardly into the tissue region surrounding the catheter. The catheter body may be porous or substantially non-porous (i.e. still permits sufficient diffusion of the lower alcohol, typically from a distal tip of the catheter into the tissue region surrounding the tip). While the use of such catheter bodies can be beneficial with many anti-microbial locking solutions, such as that taught in U.S. Pat. No. 5,077,281, the full disclosure of which has been incorporated herein by reference, it is particularly useful with the lower alcohols of the present invention. It will be appreciated that the lower alcohols have relatively low molecular weights and polar structures which will enable them to readily penetrate into and optionally through many porous or partially porous materials. Exemplary porous materials for construction of the catheter body include silicone rubber, expanded PTFE (e.g., GORE-TEX®, medical membranes) and the like. Such materials may be formed into the tubular catheter bodies or may be incorporated as separate component(s) into the catheter bodies.

In a first aspect, a locking composition for filling an implantable catheter comprises at least one lower alcohol in a range from 1% to 99% by volume and at least one other anti-microbial or anti-coagulant compound in a range from 1% to 99% by volume. The lower alcohol is selected from the group consisting of ethanol, propanol, and butanol, with the presently preferred alcohol being isopropanol. The lower alcohol will usually be in aqueous solution, typically at 1% to 99% by volume, usually from 5% to 95% by volume. The at least one other anti-microbial is selected from the group consisting of taurolidine and triclosan, and the at least one anti-coagulant is selected from the group consisting of riboflavin, sodium citrate, ethylene diamine tetraacetic acid, and citric acid. The implantable catheter may be a transcutaneous catheter attached at its distal end to a body lumen, typically a blood vessel, the peritoneal cavity, or the like. Alternatively, the implantable catheter may be a subcutaneously implantable catheter which is attached at its distal end to a blood vessel, the peritoneal cavity, or the like. The locking composition may be used with porous or substantially non-porous catheter bodies, as described above.

In a second aspect, a locking composition comprises one lower alcohol in a range from 1% to 99% by volume and at least one other anti-microbial or anti-coagulant compound in a range from 1% to 99% by volume. The lower alcohol is selected from the group consisting of ethanol, propanol, and butanol, with isopropanol being the preferred alcohol. The at least one other anti-microbial is selected from the group consisting of taurolidine and triclosan, and the at least one anti-coagulant is selected from the group consisting of riboflavin, sodium citrate, ethylene diamine tetraacetic acid, and citric acid. A preferred concentration of the anticoagulant is about 4% by volume. Most preferably, the concentration of the locking composition comprises isopropanol by about 17.5% volume and sodium citrate by about 4% weight to volume.

In a third aspect, a method according to the present invention for disinfecting an implanted catheter comprises introducing an anti-microbial solution into a lumen of the catheter, wherein at least a portion of the catheter permits sufficient diffusion of the anti-microbial solution outwardly from the lumen into the catheter body, and preferably into tissue surrounding the catheter to eradicate an existing infection. Exemplary and preferred anti-microbial solutions include at least one lower alcohol, preferably ethanol, propanol, or butanol, and most preferably isopropanol. The solution may further comprise at least one other anti-microbial, preferably taurolidine or triclosan, or anti-coagulant compound, preferably riboflavin, sodium citrate, ethylene diamine tetraacetic acid, or citric acid, as described above. The implanted catheters may be subcutaneously or transcutaneously implanted.

In a forth aspect of the present invention, a kit for disinfecting an implantable catheter comprises a container (optionally a syringe) holding a volume of a solution of a lower alcohol and instructions for use. The instructions set forth a method comprising introducing the solution into a lumen of the catheter, wherein at least a portion of the catheter permits sufficient diffusion of the solution outwardly from the lumen into the catheter body, and preferably into tissue surrounding the catheter to eradicate an existing infection. The kit may further comprise a package for holding both the container and the instructions for use, such as a box, tray, tube, pouch, or the like. The lower alcohol is typically selected from the group consisting of ethanol, propanol, and butanol, with isopropanol being the preferred alcohol. The volume of the solution in the container is typically in the range from 1 ml to 20 ml, preferably from 2 ml to 10 ml, usually being about 2 ml to 4 ml. Additionally, the container will usually comprise a syringe to permit direct introduction of the solution into the implantable catheter.

BRIEF DESCRIPTION OF THE DRAWINGS

FIGS. 1A and 1B illustrate methods according to the present invention for locking and disinfecting a transcutaneous catheter.

FIGS. 2A–2C illustrate methods according to the present invention for locking and disinfecting a subcutaneously implanted catheter.

DESCRIPTION OF THE SPECIFIC EMBODIMENTS

Figure 2B:
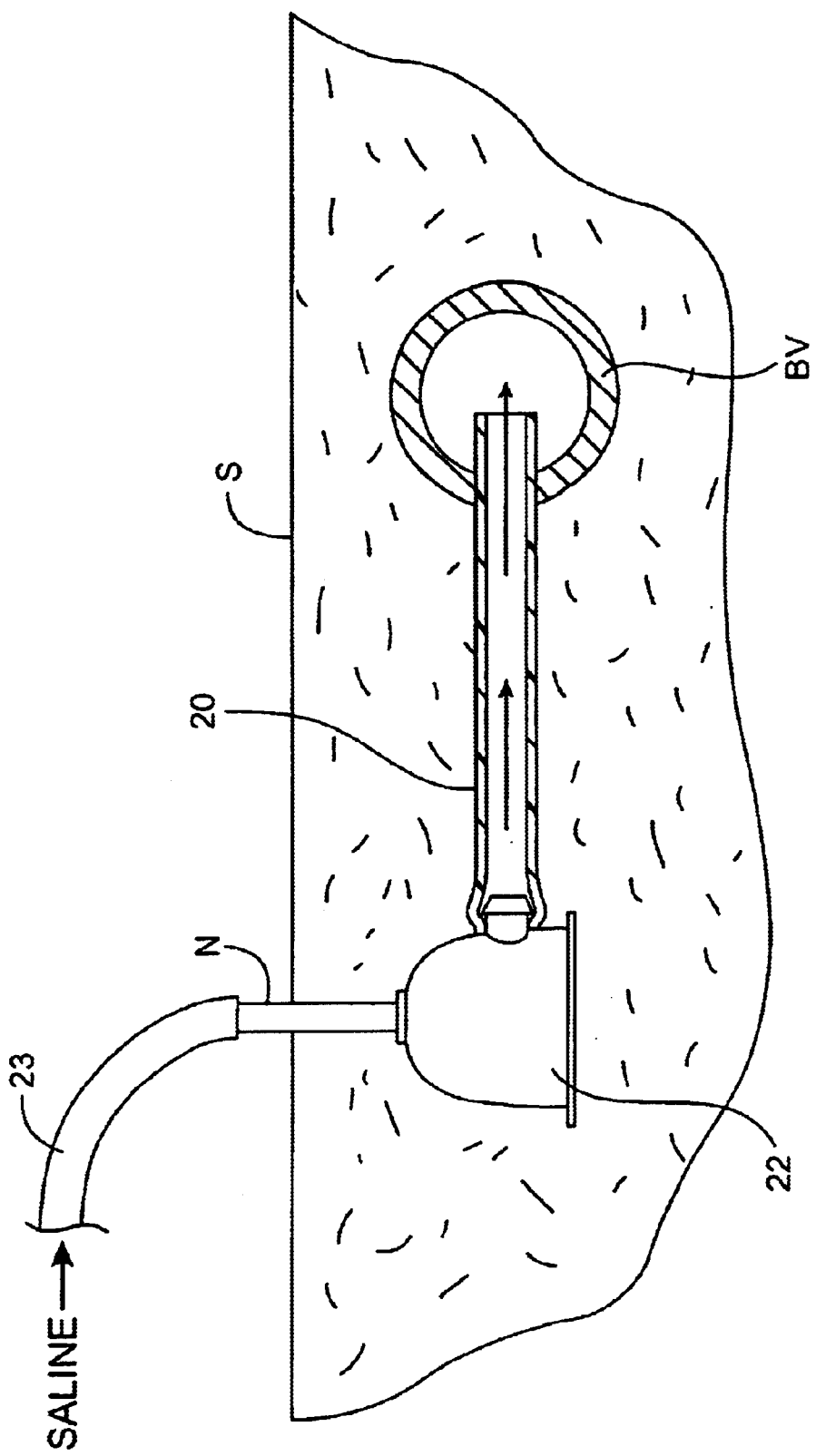

Referring now to FIGS. 1A and 1B, a method according to the present invention for locking a transcutaneously implanted venous catheter 10 will be described. The venous catheter 10 will be implanted through a patient's skin S into a vein V for infusion of the patient. When it is desired to disconnect the patient from the source of infusion, it will be necessary to lock the catheter to inhibit plugging and fouling caused by coagulation, and preferably to further eradicate existing infection and/or inhibit the risk of infection. Shown in FIG. 1A, a tube 12 containing an IV solution will normally be connected to the proximal hub 14 of the catheter 10. The IV line 12 will be disconnected, and the catheter 10 usually flushed with saline or other flushing solution. After the flushing is completed, a solution of a lower alcohol and an additive can be introduced to fill the inner lumen of the catheter 10, as shown in FIG. 1B. Usually, a sufficient volume of the solution (as set forth above) will be introduced to completely fill the lumen, with minimum excess passing from distal end 16 of the catheter. The loss of excess solution into a blood vessel or most other body lumens, however, will generally not be a problem. The "column" of the solution will then occupy the inner lumen, and the proximal hub 14 will be sealed, helping retain the solution in place. It has been found that the solution of the lower alcohol with the additive will effectively inhibit clotting and coagulation at the distal end 16 as well as to eradicate existing infections and/or inhibit potential infections throughout the catheter. When it is desired to reattach the patient to the IV source, the solution will be removed and the catheter lumen flushed with saline.

The locking composition for filling the implantable catheter typically comprises at least one lower alcohol and at least one other anti-microbial or anti-coagulant compound. Preferred compositions include lower alcohol in the range between about 1% to 99% with taurolidine in the range between about 1% to 99%, lower alcohol in the range between about 1% to 99% with triclosan in the range between about 1% to 99%, lower alcohol in the range between about 1% to 99% with riboflavin in the range between about 1% to 99%, lower alcohol in the range between about 1% to 99% with sodium citrate in the range between about 1% to 99%, lower alcohol in the range between about 1% to 99% with ethylene diamine tetraacetic acid in the range between about 1% to 99%, and lower alcohol in the range between about 1% to 99% with citric acid in the range between about 1% to 99%. Saline, water, or standard heparin solution may also be added to any of the above described compositions.

Referring now FIGS. 2A–2C, locking of a subcutaneously implanted catheter 20 used for hemodialysis access will be described. The catheter 20 is implanted between a target blood vessel BV, typically a vein, and an implanted port 22. During hemodialysis, blood may be withdrawn through the catheter 20, through the port 22 and externally through a needle N and connecting line 23 used to percutaneously access the port 22. Alternatively, the port and catheter could be used to return treated blood to the patient. As described in the copending applications incorporated by reference above, the port and catheter combinations are typically used in pairs to permit both blood withdrawal and blood return.

Figure 2C:
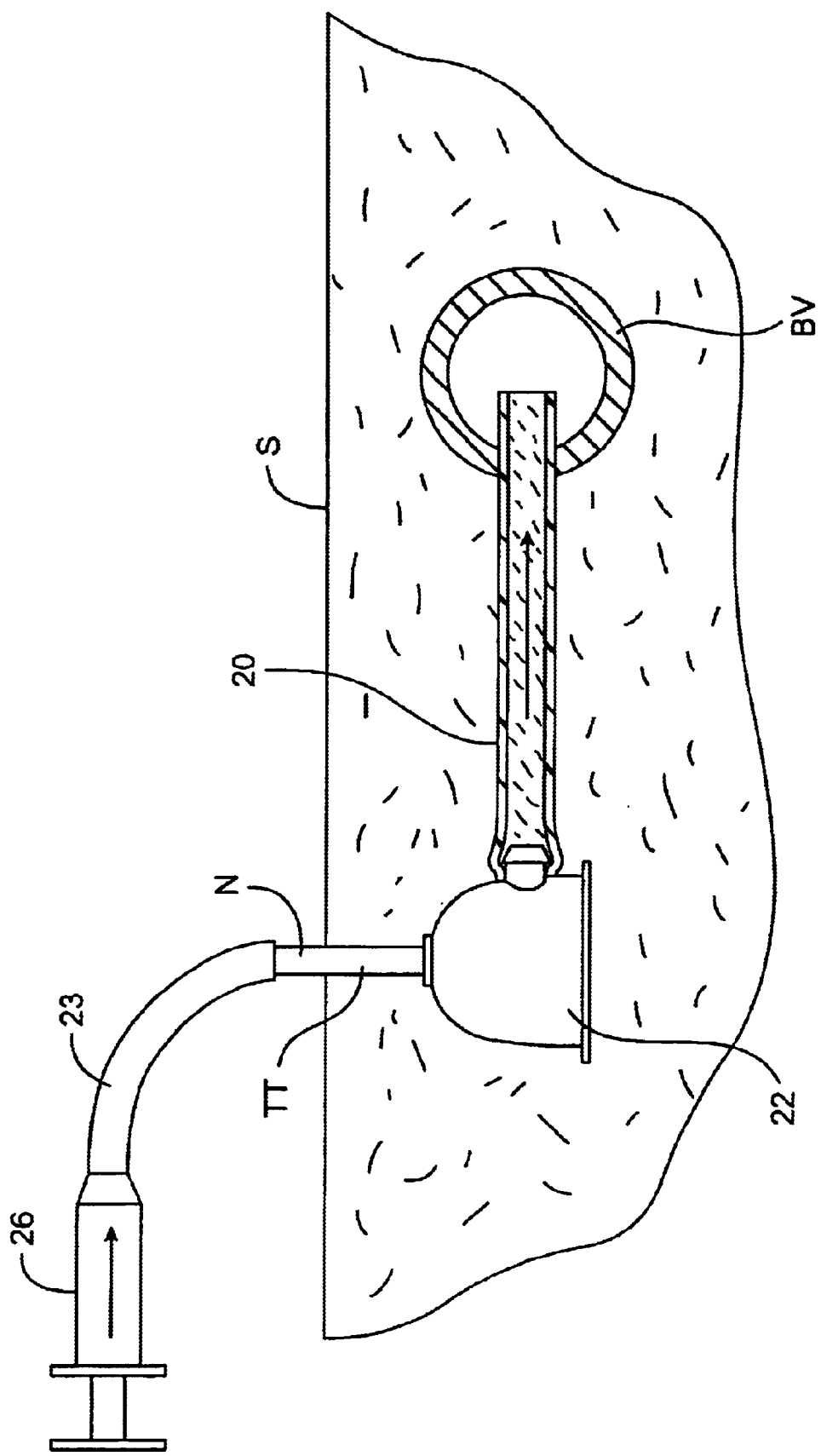

When it is desired to end a hemodialysis (or hemofiltration) treatment, saline will be introduced through the needle N (typically from a syringe which is attached to the connecting line 23) to flush the lumen, as shown in FIG. 2B. After the flush is complete, a container such as syringe 26 containing the solution of the lower alcohol with an additive is injected through the port 22/line 23 and into the lumen of catheter 20 to displace the saline and lock the catheter. The solution will remain in place within the catheter 20 after the needle end is withdrawn and the valve 22 closed to seal off the proximal end of the catheter 20. As a particular advantage, residual solution in the needle will be dispersed in the tissue tract TT left by the needle as well as in portions of the port 22 upstream of its internal valve. The presence of the alcohol or other anti-microbial additives in the solution will further eradicate existing infections and/or inhibit potential infections in both the port and tissue tract.

Figure 3A:
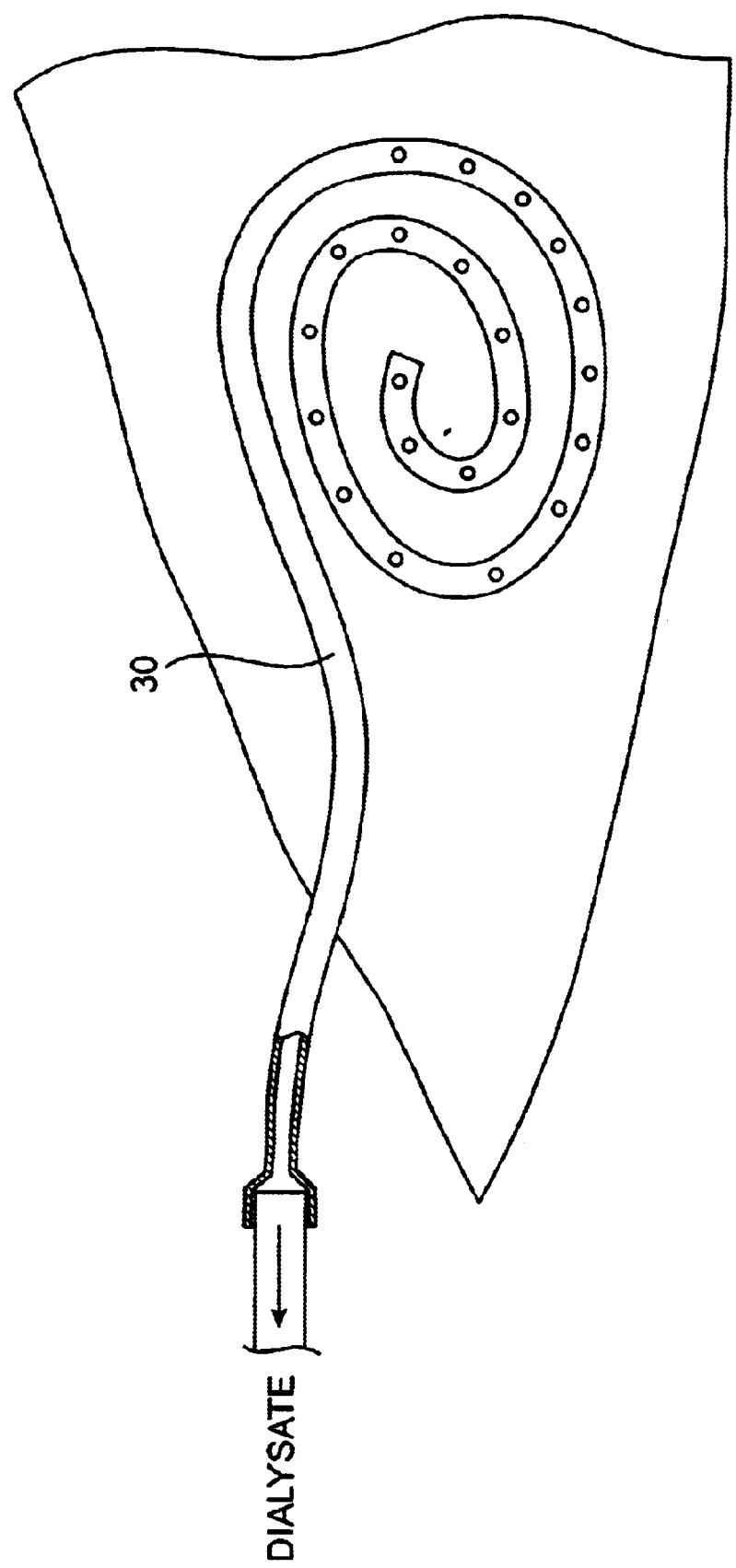
FIGS. 3A–3C illustrate methods according to the present invention for locking and disinfecting a peritoneal dialysis catheter.
Figure 3B:
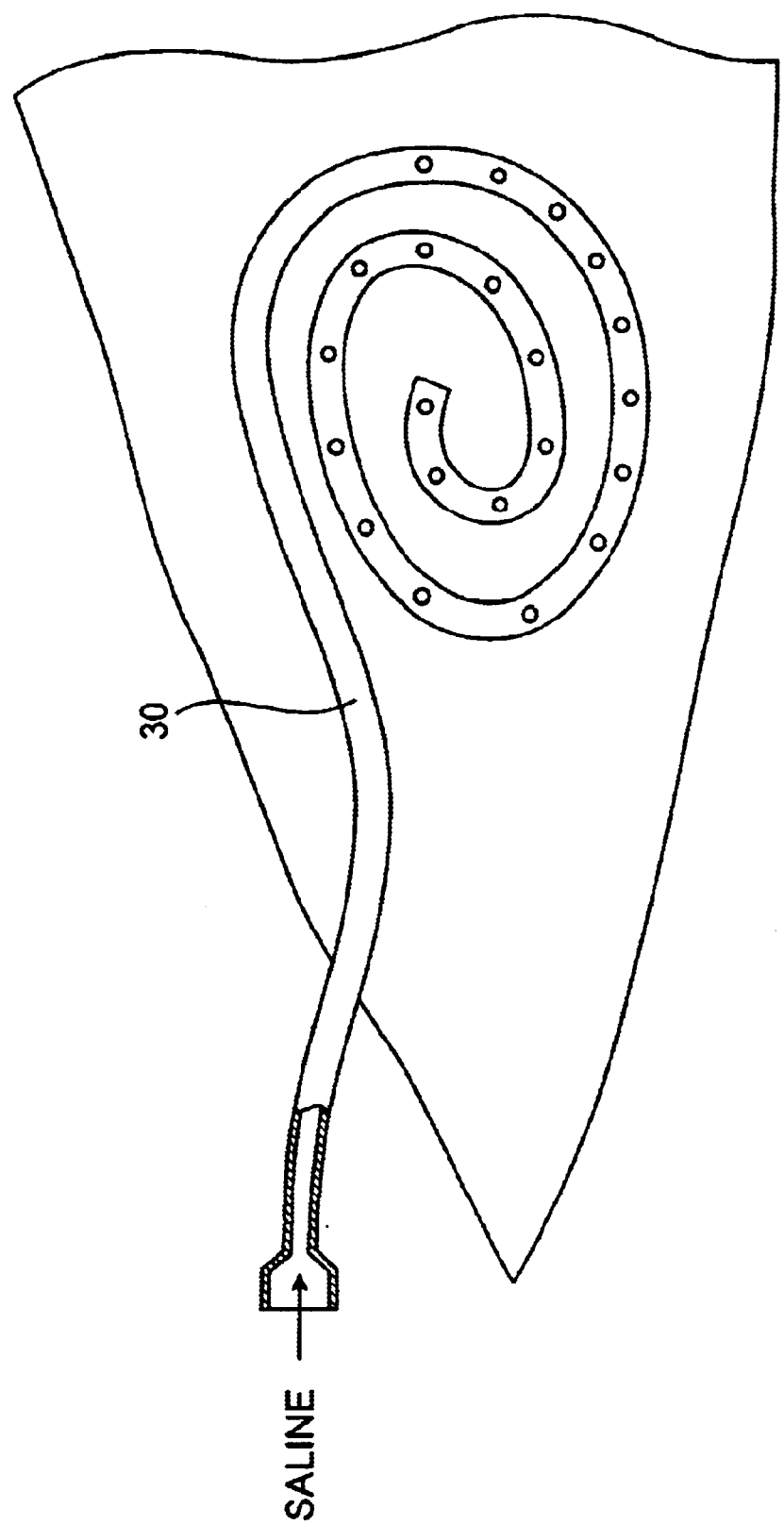
Figure 3C:
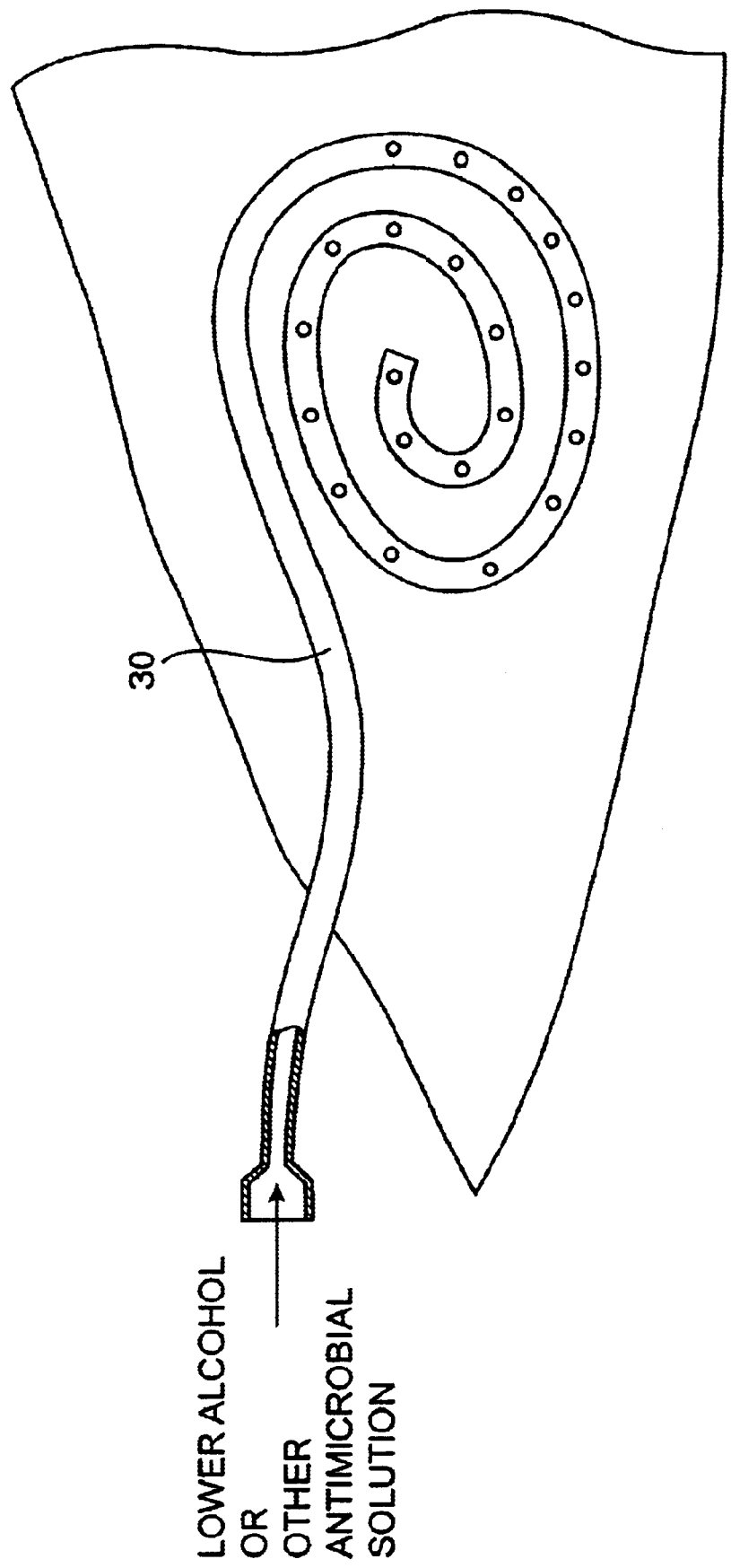

The methods of the present invention may also be used to lock non-vascular catheters, such as peritoneal dialysis catheters 30, as shown in FIGS. 3A–3C. After a peritoneal dialysis treatment, the used dialysate will be withdrawn from the catheter 30, as shown in FIG. 3A. After the dialysate has been sufficiently removed, the dialysis catheter 30 may optionally be flushed with saline, as shown in FIG. 3B. After flushing, the solution of the lower alcohol with the additive is introduced to the peritoneal dialysis catheter 30, as shown in FIG. 3C, so that it fills the lumen of the catheter, as described previously with the vascular catheters. The use of an alcohol lock with an additive for peritoneal dialysis catheters is particularly advantageous in eradicating existing infections and/or inhibiting potential infections.

Figure 4:
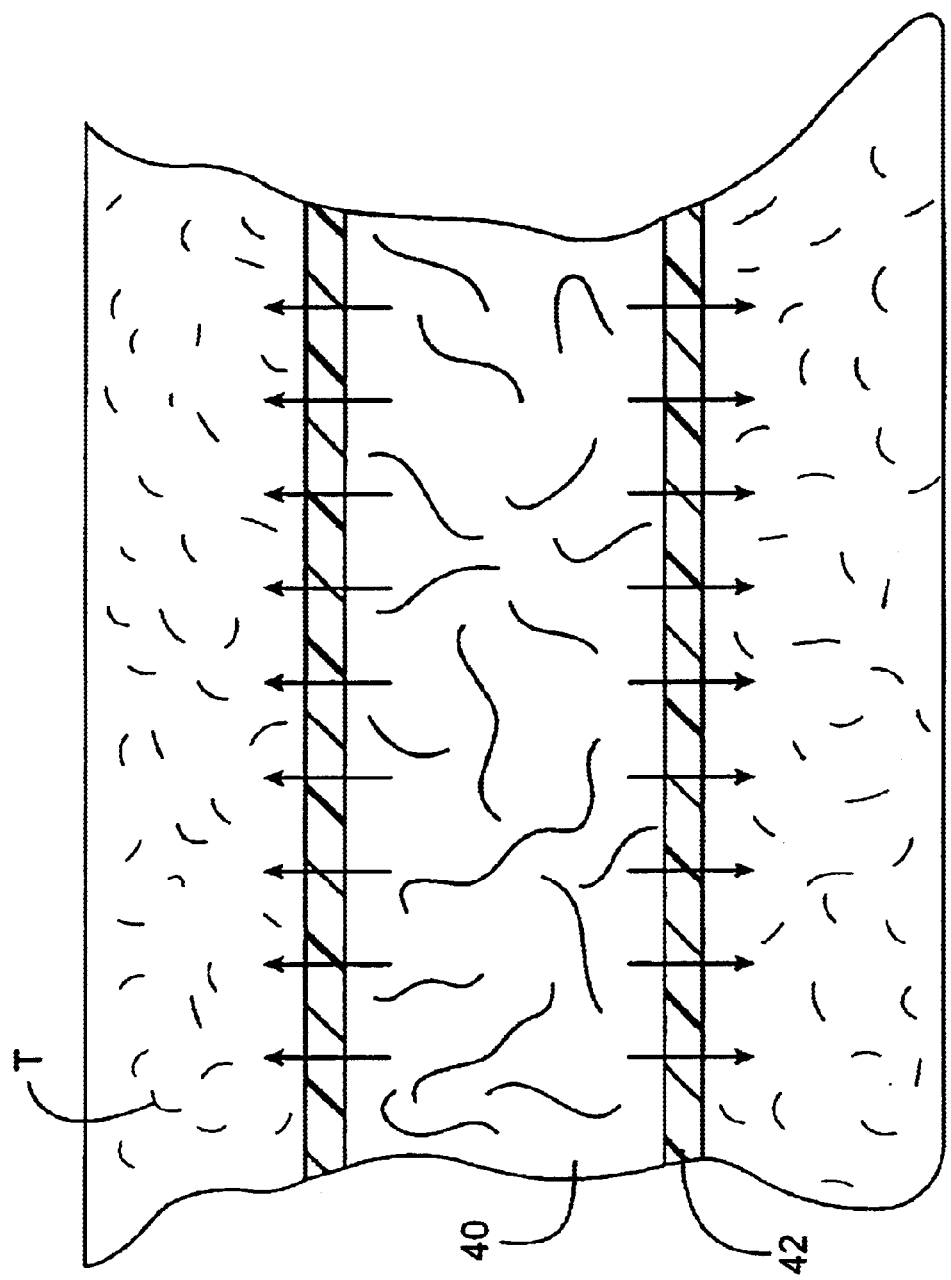
FIG. 4 illustrates a preferred aspect of the present invention where an anti-microbial locking fluid permeates into an implanted catheter body and preferably into the tissue surrounding the catheter body.

Referring now to FIG. 4, the use of lower alcohols for disinfecting a catheter can be enhanced by utilizing an implanted catheter where at least a portion of the catheter body permits the lower alcohol to permeate the catheter body. When the lumen 40 of the catheter body 42 is filled with a solution of a lower alcohol, the solution will be able to penetrate into the catheter body and preferably outwardly into the tissue T surrounding the catheter, as shown by the arrows in FIG. 4. As described above, the catheter body may be porous or substantially non-porous (i.e. still permits sufficient diffusion of the lower alcohol into the tissue region typically surrounding a distal tip of the catheter). Thus, the anti-microbial properties of the solution will not be limited to the interior lumen of the catheter, but will also be effective on a surface or distal tip of the catheter and in the tissue region immediately surrounding the catheter body to eradicate existing infections and/or inhibit potential infections. Particularly suitable porosity properties for the catheter bodies have been set forth above. The solution may further incorporate any of the anti-microbial or anti-coagulant compounds described above.

Figure 5:
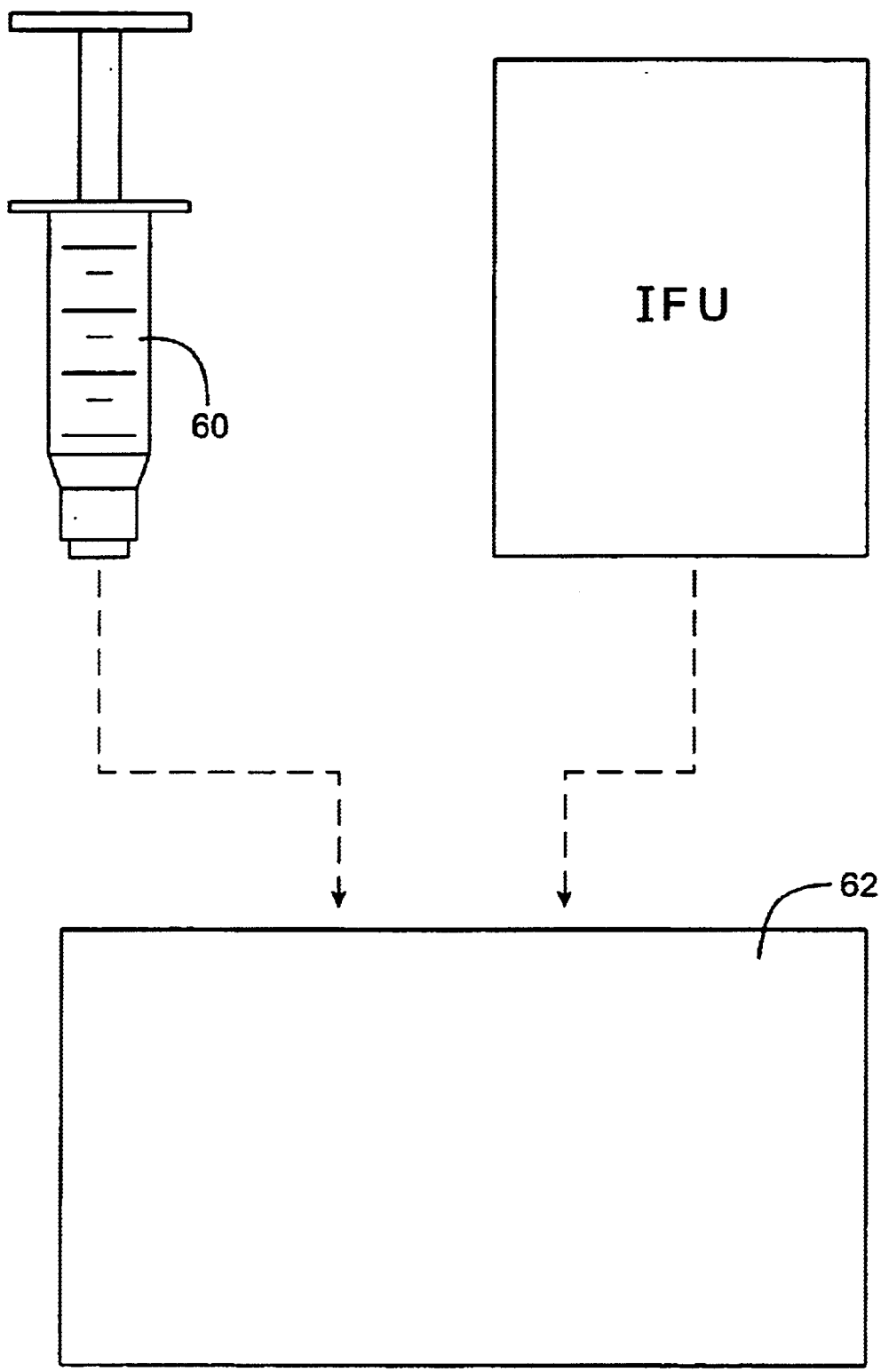
FIG. 5 illustrates a kit constructed in accordance with the principles of the present invention.

Referring now to FIG. 5, kits according to the present invention will comprise at least a container 60, such as a syringe, for holding a volume of the solution of the lower alcohol. The volume will typically be within the ranges set forth above. In addition, the kit will contain instructions for use (IFU) setting forth a method for disinfecting an implanted catheter by introducing the solution into a lumen of the catheter, wherein at least a portion of the catheter permits sufficient diffusion of the solution outwardly from the lumen into the catheter body, and preferably into tissue surrounding the catheter to eradicate an existing infection. Usually, the kits will further contain a package 62, such as any conventional medical device package, including boxes, tubes, trays, pouches and the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An implantable catheter filled with a locking composition, the locking composition comprising:
   at least one lower alcohol in a range from 1% to 99% by volume; and
   at least one other anti-microbial compound or at least one anti-coagulant compound in a range from 1% to 99% by volume.

2. An implantable catheter as in claim 1, wherein the lower alcohol is selected from the group consisting of ethanol, propanol, and butanol.

3. An implantable catheter as in claim 2, wherein the lower alcohol is isopropanol.

4. An implantable catheter as in claim 1, wherein the at least one other anti-microbial compound is selected from the group consisting of taurolidine and triclosan.

5. An implantable catheter as in claim 1, wherein the at least one anti-coagulant compound is selected from the group consisting of riboflavin, sodium citrate, ethylene diamine tetraacetic acid, and citric acid.

6. An implantable catheter as in claim 5, wherein the at least one anti-coagulant compound is riboflavin at about 4% by volume.

7. An implantable catheter as in claim 5, wherein the at least one anti-coagulant compound is sodium citrate at about 4% by volume.

8. An implantable catheter as in claim 5, wherein the at least one anti-coagulant compound is ethylene diamine tetraacetic acid at about 4% by volume.

9. An implantable catheter as in claim 5, wherein the at least one anti-coagulant compound is citric acid at about 4% by volume.

10. An implantable catheter as in claim 1, wherein the implantable catheter is a subcutaneous catheter implantable between a subcutaneous port and a body lumen.

11. An implantable catheter as in claim 10, wherein the catheter is open to blood flow in a blood vessel.

12. An implantable catheter as in claim 10, wherein the catheter is open to a peritoneal cavity.

13. An implantable catheter as in claim 10, wherein the locking composition is introducible with a needle that disperses the composition in the port and tissue tract leading to the port as the needle is withdrawn from the port.

14. A locking composition comprising:
   at least one lower alcohol in a range from 1% to 99% by volume, wherein the lower alcohol is isopropanol; and
   at least one anti-coagulant compound in a range from 1% to 99% by volume, wherein the anti-coagulant compound is sodium citrate or citric acid.

15. A composition as in claim 14, wherein the at least one anti-coagulant compound is sodium citrate at about 4% by volume.

16. A composition as in claim 14, wherein the at least one anti-coagulant compound is citric acid at about 4% by volume.

17. A locking composition comprising:
   at least one lower alcohol in a range from 1% to 99% by volume; and
   at least one anti-coagulant compound in a range from 1% to 99% by volume, wherein the at least one anti-coagulant compound is riboflavin.

18. A composition as in claim 17, wherein the at least one anti-coagulant compound is riboflavin at about 4% by volume.

19. A locking composition comprising:
   at least one lower alcohol in a range from 1% to 99% by volume; and
   at least one other anti-microbial compound in a range from 1% to 99% by volume, wherein the at least one other anti-microbial compound is taurolidine.

20. A composition as in claim 19 or 17, wherein the lower alcohol is selected from the group consisting of ethanol, propanol, and butanol.

21. A composition as in claim 20, wherein the lower alcohol is isopropanol.

22. A method for disinfecting an implanted catheter, said method comprising:
   introducing an anti-microbial solution to a lumen of the catheter, wherein at least a portion of the catheter permits sufficient diffusion of the anti-microbial solution outwardly from the lumen into (issue surrounding the catheter to eradicate an existing infection, the anti-microbial solution comprising at least one lower alcohol and at least one other anti-microbial compound or at least one anti-coagulant compound in a range from 1% to 99% by volume.

23. A method as in claim 22, wherein the lower alcohol is selected from the group consisting of ethanol, propanol, and butanol.

24. A method as in claim 23, wherein the lower alcohol is isopropanol.

25. A method as in claim 22, wherein the other antimicrobial compound is selected from the group consisting of taurolidine and triclosan.

26. A method as in claim 22, wherein the at least one anti-coagulant compound is selected from the group consisting of riboflavin, sodium citrate, ethylene diamine tetraacetic acid, and citric acid.

27. A kit for disinfecting an implantable catheter, said kit comprising:
   a container holding a volume of a solution comprising a lower alcohol and at least one other anti-microbial compound or at least one anti-coagulant compound in a range from 1% to 99% by volume; and
   instructions for use setting forth a method comprising introducing the solution to a lumen of the catheter, wherein at least a portion of the catheter permits sufficient diffusion of the solution outwardly form the lumen into tissue surrounding the catheter to eradicate an existing infection.

28. An implantable catheter as in claim 1, wherein the implantable catheter is a transcutaneous catheter open to a body lumen.

29. An implantable catheter as in claim 28, wherein the catheter is open to blood flow in a blood vessel.

30. An implantable catheter as in claim 28, wherein the catheter is open to a peritoneal cavity.

31. A kit as in claim 27, wherein the volume is in the range from 1 ml to 20 ml.

32. A kit as in claim 27, wherein the container comprises a syringe.

33. An implantable catheter filled with a locking composition, the locking composition comprising:
   at least one lower alcohol in a range from 1% to 99% by volume; and
   at least one additive in a range from 1% to 99% by volume;
   wherein the implantable catheter is a transcutaneous catheter open to a body lumen.

34. An implantable catheter filled with a locking composition, the locking composition comprising:
   at least one lower alcohol in a range from 1% to 99% by volume; and
   at least one additive in a range from 1% to 99% by volume;
   wherein the implantable catheter is a subcutaneous catheter implantable between a subcutaneous port and a body lumen.

* * * * *